(12) United States Patent
Scarpone (10) Patent No.: US 10,952,871 B2
(45) Date of Patent: Mar. 23, 2021

(54) SURGICAL TOOLS AND KITS FOR CARTILAGE REPAIR USING PLACENTAL, AMNIOTIC, OR SIMILAR MEMBRANES

(71) Applicant: Michael A. Scarpone, Bloomingdale, OH (US)

(72) Inventor: Michael A. Scarpone, Bloomingdale, OH (US)

(73) Assignee: Michael A. Scarpone, Bloomingdale, OH (US)

( * ) Notice: Subject to any disclaimer, the term of this patent is extended or adjusted under 35 U.S.C. 154(b) by 644 days.

(21) Appl. No.: 15/482,696

(22) Filed: Apr. 7, 2017

(65) Prior Publication Data

US 2018/0289507 A1  Oct. 11, 2018
US 2019/0388239 A9  Dec. 26, 2019

Related U.S. Application Data

(60) Provisional application No. 62/319,308, filed on Apr. 7, 2016.

(51) Int. Cl.
*A61F 2/46* (2006.01)
*A61M 29/00* (2006.01)
*A61F 2/30* (2006.01)

(52) U.S. Cl.
CPC ........ *A61F 2/4601* (2013.01); *A61F 2/30756* (2013.01); *A61F 2/4618* (2013.01); *A61M 29/00* (2013.01); *A61F 2002/30757* (2013.01); *A61F 2002/4635* (2013.01); *A61F 2002/4681* (2013.01); *A61F 2002/4685* (2013.01)

(58) Field of Classification Search
CPC .................. A61F 2002/4602; A61M 29/00
See application file for complete search history.

(56) References Cited

U.S. PATENT DOCUMENTS

| 5,171,279 A * | 12/1992 | Mathews | A61B 17/70 128/898 |
|---|---|---|---|
| 6,146,385 A * | 11/2000 | Torrie | A61B 17/1635 606/80 |
| 6,152,871 A * | 11/2000 | Foley | A61B 17/3421 600/114 |
| 2002/0157676 A1* | 10/2002 | Schmieding | A61B 17/1615 128/898 |
| 2004/0092936 A1* | 5/2004 | Miller | A61B 17/1764 606/916 |

(Continued)

*Primary Examiner* — Nicholas W Woodall
(74) *Attorney, Agent, or Firm* — K&L Gates LLP (57) ABSTRACT

Surgical tools and kits are disclosed for repairing hyaline or meniscal cartilage, using membrane segments to protect and promote the growth and activity of cartilage-generating cells. These kits include: (i) a set of dilator tubes, adapted from similar tubes used in spinal surgery except shorter, that will allow a surgeon to progressively enlarge an insertion tunnel for inserting a membrane segment into an articulating joint that is being repaired; and, (ii) an assortment of membrane "tamping" devices, with smooth rounded "tamping heads" (or tips, etc.), and with a size and length that allow the tool tip to pass through the longest dilator tube while being held by the surgeon. Additional components (including disposable supplies) that can help facilitate these types of surgery can be included in any such kit, or in "supplemental" kits that can be bundled and shipped with these "primary" kits.

16 Claims, 5 Drawing Sheets

(56) References Cited

U.S. PATENT DOCUMENTS

| | | | |
|---|---|---|---|
| 2007/0010845 A1* | 1/2007 | Gong | A61B 17/8855 606/192 |
| 2007/0055276 A1* | 3/2007 | Edidin | A61B 17/8855 606/92 |
| 2010/0274080 A1* | 10/2010 | Donovan | A61B 17/8811 600/104 |
| 2014/0257489 A1* | 9/2014 | Warren | A61B 17/1671 623/17.16 |
| 2015/0045768 A1* | 2/2015 | Schmieding | A61B 17/885 604/506 |
| 2018/0155678 A1* | 6/2018 | Francis | C12N 5/0068 |

* cited by examiner

SUCTION TOOL FOR MEMBRANE INSERTION

Fig. 5

INFLATABLE ENVELOPE FOR TAMPING

SURGICAL TOOLS AND KITS FOR CARTILAGE REPAIR USING PLACENTAL, AMNIOTIC, OR SIMILAR MEMBRANES

RELATED APPLICATION

This application claims priority under 35 USC 119(e) based on provisional application 62/319,308, filed on Apr. 7, 2016.

BACKGROUND

This invention is in the field of disposable supplies and equipment for use during specialized types of orthopedic surgery and "sports medicine".

Extensive work has been done by surgeons and researchers to develop ways to treat and repair damaged hyaline and meniscal cartilage in articulating joints. Articulating joints include joints in which two relatively thin layers of cartilage (which cover specialized bone surfaces called "condyles") press and slide against each other, in a manner which is lubricated by synovial fluid (accordingly, articulating joints also are called synovial joints). Articulating joints include knees, hips, shoulders, elbows, ankles, wrists, fingers, etc. They exclude spinal joints and spinal discs, which contain a very different type of cartilage that prevents, rather than enables, sliding motion, since sliding motion involving spinal discs would severely damage the spinal cord. In addition, the types of cartilage that are present in noses, ears, and windpipes are excluded from any discussion or coverage herein, since those types of cartilage are not involved in the types of "articulating" motion that involve compression and sliding.

Hyaline and meniscal cartilage do not have a normal blood supply, and if they become damaged due to injury or disease, they have only a very limited (and in most cases inadequate) ability to regrow, regenerate, or repair themselves, in ways comparable to other types of bodily tissues or bones. Accordingly, the various approaches that have been developed for surgically repairing and/or replacing damaged cartilage, in articulating (synovial) joints, can be divided into two main categories, which can be referred to as either mechanical or biological methods.

As suggested by the name, mechanical methods generally involve: (i) removal of the damaged cartilage, and (ii) replacement with a mechanical device. These types of operations are exemplified by conventional knee replacement implants (which are used in a type of surgery that is often referred to as "total knee replacement" or "TKR" surgery), and conventional hip replacement implants. In either situation, two cartilage segments will be involved, and in nearly all cases, both segments will need to be replaced, since a damaged surface on either segment will quickly begin to abrade and damage the other cartilage segment which the damaged surface presses and slides against. Accordingly, when damaged knee cartilage must be repaired by means of a "total knee replacement", the cartilage segments (as well as a segment of supporting bone, directly beneath the hyaline cartilage layers) on both the "femoral runner" (i.e., at the bottom end of the thigh bone) and the "tibial plateau" (i.e., at the top end of the shin bone) usually must be repaired, and the surgeon will decide whether to also replace the patellar (kneecap) cartilage during that same operation.

In contrast, biological methods for cartilage repair that are of interest today involve transplanting certain types of specialized cells (usually harvested from elsewhere in the body of the same patient, to avoid rejection by the immune system) directly onto a damaged cartilage surface. The types of cells that are used for these types of purposes are able to generate and secrete the specialized types of collagen that create the main structures of hyaline or meniscal cartilage. Several such types of cells are known, and they include cells referred to as mesenchymal cells, subchondral cells, and "bone marrow stem cells". If desired, any of these types of cells can be called "stem cells" or "precursor cells", since they are "partially differentiated" cells that can be induced, by certain types of known hormones, to rapidly complete a "maturation process" that will cause them to convert, fully and finally, into cartilage-generating cells. Alternately, they can be referred to as "stromal precursor cells"; the root word "stroma" refers to "structural", and "stromal precursor cells" have reached a stage of differentiation where they can mature into any of various types of "structural" cells, including the types of cells that can help regenerate cartilage.

Accordingly, most biological approaches for repairing cartilage usually involve the following steps:

(1) harvesting a batch of cells that will contain a substantial number of one of more types of stem (precursor) cells that can mature into cartilage-generating cells. This can be done via a "bone marrow aspiration", which uses a relatively large needle that is inserted into the marrow region inside a large bone, such as the pelvic bone, usually under local anesthesia;

(2) treating the aspirated cell mixture, in one or more ways that will concentrate the stem cells from the initial batch of cells while reducing unwanted materials (such as extracellular fat, lymph fluid, and unwanted types of cells);

(3) contacting the concentrated stem cell preparation with at least one hormone which will help convert the semi-mature stem cells into cells that will actively generate and secrete the type of collagen fibers that form hyaline or meniscal cartilage; and, (4) implanting the hormone-treated cells into the damaged joint, in a manner that will be intended to cause the cells to be positioned in the desired location, and to remain in that location for a sustained period of time, even after the repaired cartilage segment is subjected to compressive loadings and sliding-type motion.

A recent medical advance has created a new and apparently improved way to help surgeons achieve the fourth numbered step listed above (i.e., emplacing the hormone-treated cells on a damaged cartilage surface, in a manner that will help them stay in that targeted location, even after the cartilage segment is subjected to compressive loadings and sliding-type motion). That advance involves the use of certain types of membranes that can be harvested from human placentas, and/or from the so-called "amniotic sac" which surrounds and encloses both the fetus, and the amniotic fluid which surrounds the fetus, inside a mother's womb (i.e., uterus).

The placenta is the mass of tissue (occasionally referred to as "the only disposable mammalian organ") which forms the interface between a growing fetus, and the internal surface of the maternal womb/uterus. In a normal and healthy childbirth, the placenta detaches from the uterine wall soon after the baby is born, and it is then expelled from the uterus (usually with the aid of a surgeon or midwife exerting a gentle tugging force on the umbilical cord) as a generally gelatinous mass of tissue (which is often called "the afterbirth"). In most births, it is simply discarded, as a form of medical waste. However, some years ago, some researchers and companies began analyzing and experimenting with placental tissue, motivated by the realization that it contains a rich supply of "multi-potent" and even some "omni-potent" (or "toti-potent") stem cells that might become very useful, for various medical and biological purposes, if harvested and processed carefully. Furthermore, research into placental tissue also disclosed that it is generally shielded and protected against attack by a host's immune system, if it is transplanted into some other adult human. This is entirely logical, within the field of biology, since otherwise, any embryo that begins to grow within any female might otherwise be recognized (and then attacked) as a foreign invader, by the mother's immune system.

The amniotic sac is classified as a type or category of placental tissue, by doctors; therefore, amniotic membranes are included within any references to placental tissues or membranes.

Similarly, the umbilical cord also is a type or category of placental tissue. Therefore, any membranes derived from an umbilical cord also are included within any references to placental tissues or membranes.

Accordingly, various types of membrane segments derived from placental tissues (including amniotic or umbilical membranes, as noted above) can be harvested and treated in ways that render them potentially useful for tissue transplant recipients. Several companies have been created which specifically sell placental membranes for use in surgery; examples include Skye Biologics Inc. (skyebiologics.com); Amniox Medical Inc. (amnioxmedical.com); MiMedx Group Inc. (mimedx.com); Alliqua BioMedical Inc. (alliqua.com); Osiris Therapeutics Inc. (osiris.com); Applied Biologics Inc. (appliedbiologics.com), Burst Biologics LLC (burstbiologics.com), and BioD LLC (biodlogics.com). In addition, relevant articles have begun to appear in the medical literature, including 2 recent review articles (Riboh et al 2016, and McIntyre et al 2017), which review and describe various reports on early efforts to test and use placental membranes to repair tendon or ligament injuries in adults.

Another class of tissue-repair membranes that also merit evaluation and testing for this type of use can be called "collagen-derived" membranes. These types of membranes can be manufactured by using, as a starting material, collagen fibers from a natural source. Since collagen is the fibrous extra-cellular protein that holds together soft tissues in all mammals, large supplies of collagen are readily available in tissues that can be harvested, in sanitary conditions, in specialized tissue-harvesting facilities that can be installed in slaughterhouses that process cattle or pigs. As just one example, the Stryker company (stryker.com) sells "TissueMend Soft Tissue Repair Matrix" membranes, with collagen obtained from tendons in cow legs, for use in treating injured tendons or ligaments. Accordingly, any such membrane with biologically-derived collagen which has been shown to be useful in helping heal and regenerate one or more types of wounds or injuries, in mammals, can be used with the types of tools and devices described herein.

Most current uses for placental and/or collagen-derived membranes in human patients involve treating chronic softtissue wounds or defects, such as lingering skin ulcers, urological repairs, and repairs for injured tendons or ligaments. However, a few researchers recently have begun trying to extend the use of placental or similar membranes into a new and different medical field, involving the repair of hyaline cartilage in articulating joints. As of early 2016, all such research involving cartilage repair, as reported in respected medical journals, apparently has been limited to animal tests. Examples of such reports include Garcia et al 2014 (tested on sheep), Liu et al 2014 (tested on rats), and Nogami et al 2016 (tested on rats); all of those tests involved knee joints, since cartilage surfaces inside knee joints are close to the outer skin surface, and are relatively easy to access and manipulate. All of those reports (and various others in the field of cartilage repair) indicate promising results, but they also indicate that this particular line of research will need a great deal of additional testing and evaluation, before it is ready to be seriously proposed and considered for clinical trials on humans.

Despite the very early and exploratory status of that work, it has drawn the attention of the Applicant herein, a surgeon and Doctor of Osteopathy who specializes in the branch of medicine that has become widely known as "sports medicine." He is the Team Physician for two different professional teams (in two different sports) that compete at the highest levels of professional sports in the US, and he has devoted a large part of his career to searching for the best possible ways to use various types of stem (precursor) cells to help professional athletes, and regular people, recover and regain strength, mobility, and unimpaired performance as quickly as possible, after injuries. Accordingly, based on his knowledge of how different types of precursor cells work, and how they can and should be handled in arthroscopic surgery and "sports medicine", he already has become convinced that placental membranes offer great promise in treating injured or diseased cartilage, if the right types of tools and techniques can be developed to enable their optimal use and application (and that is the focus and purpose of this invention).

As a brief digression, the medical specialty called "sports medicine" focuses on treating muscles, joints, bones, and other structural tissues (as distinct from internal organs) in ways that minimize cutting, as much as possible, and that uses tools such as needles, syringes, and thin tubes as much as possible, rather than blades or cutting. Cutting through any soft tissue or bone (even when done with highly specialized tools and instruments, as in arthroscopic surgery) will always and inevitably disrupt the vasculature (i.e., the complex network of blood vessels, including capillaries and other "micro-vasculature" components that are too small to see without magnification), as well as nerve fibers and the neuromuscular interfaces that are present in the affected tissues. The tissue damage and disruption caused by cutting can be minimized (and in many cases avoided completely) if the same or similar results can be obtained by using hypodermic needles, syringes, and similar "minimally invasive" devices to withdraw and/or emplace fluids or fluidized materials (including cell preparations which are so densely packed that they may have a paste-like consistency) from (or into) precisely targeted locations.

As a rule of thumb, a needle puncture can and will heal within a day or two, completely, and with essentially no lasting damage of any sort, so long as it was performed properly. By contrast, if an injured tissue site that includes muscles, tendons, and ligaments must be cut open, by a scalpel blade, the site will take at least a week (and often much, much longer) to heal; and, because of factors such as scar tissue formation and misalignment of collagen fibers that had to be severed and then "rejoined by approximation", the complex arrangement of muscles, tendons, and ligaments at that site will almost never will heal as strongly and as "properly" as they were, in their pre-injured, pre-cut condition.

Accordingly, the Applicant is working at the forefront of efforts to develop and adapt new discoveries into supplies, equipment, and methods that will make it easier for hundreds or even thousands of surgeons and other doctors to begin using new types of tools and agents, quickly, efficiently, and in ways that will minimize the damage caused by outdated, no-longer-optimal surgical methods, as well as the risks and frequencies of oversights, errors, and other problems that arise when outdated, non-optimal surgically-invasive procedures are used.

One of the most common and well-known ways to accomplish that goal is through devices called "surgical kits", or simply "kits". These devices (which fall with the "article of manufacture" category in patent terminology, and which can also be called assemblies, assemblages, packaged (or sealed) assemblages, etc.) typically gather together all of the disposable supplies and reagents that a surgeon will need, in order to perform a specific type of surgical and/or injection procedure, as well as any items or supplies that a typical surgical clinic and/or operating room would not routinely have on hand. All of those components are gathered together in one or more watertight, airtight, sterile, sealed envelopes. In essentially all cases, unless a specific need compels some other arrangement, any surgical kit will have a clear plastic sheet on its upper surface, and all of the items will be arrayed in a clear and organized manner beneath that clear layer, so that a surgeon or assistant can clearly see everything that is contained in that particular kit, before opening it (which loses the assurance of sterility, and which would effectively render a kit worthless if it must be returned to the manufacturer or distributor, in opened form).

Those common traits apply to essentially all types of surgical kits. However, after that set of shared traits passes into the background, any other traits that apply to surgical kits designed for specific usages can vary widely. Some types of kits can be mass-manufactured, and can have shelf-lives of months or even years, while some other types of kits (such as kits that contain viable cells, membranes, or other biologic materials) must be custom-manufactured, and must be assembled, packaged with dry ice to keep certain components frozen, shipped via urgent delivery methods, and used within (for example) 18, 24, or 48 hours, depending on the types of cells or other biologic materials. Indeed, some kits can be completely unique, and can include cells or tissues that were harvested a few days earlier from the same patient who will then receive them back again, in modified form; those types of kits can be custom-assembled by a specialist at a high-tech specialty laboratory, based on detailed discussions with the surgeon who will be performing the procedure, to enable a single specific operation on a known individual patient. The common thread, in determining whether something falls within the industry definition of "surgical kit", is whether a set of components, tools, supplies, reagents, compounds, or other materials or devices, is gathered together within one or more sealed sterile packages which are designed and intended to render it easier for a surgeon to make sure that all of the supplies, tools, reagents, or other non-standard items that the surgeon is likely to need, while performing some specific procedure, are on hand and readily available at the start of a surgical procedure.

Based on his past experiences, encounters, and expertise in this field (which include performing numerous operations of this same general type, but with different types of biological materials), the Applicant herein has recognized that:

(i) certain types of tools adapted from other fields of orthopedic surgery (notably including spinal surgery, which is very different from knee surgery; almost no surgeons attempt to perform both types of surgery) could become very useful, if modified in ways that would render them better-suited for use in surgery involving articulating joints and hyaline cartilage, rather than spines; and, (ii) certain additional types of tools also should be added to and included within the types of kits contemplated herein, to make it easier for surgeons to handle and emplace segments of placental membranes, and possibly other types of membranes that may be discovered and/or developed in the future for promoting the transplantation of cartilage-generating cells into articulating joints.

Prior to listing the objects of this invention, several items of terminology should be addressed briefly.

"Surgery" (and any related terms, such as surgical, surgeon, etc.) are used herein to refer to any type of medical procedure that is used to repair hyaline or meniscal cartilage, if the procedure involves the manipulation of one or more types of cohesive tissue (such as a segment of placental membrane) or tissue substitute (such as a synthetic membrane which is designed and manufactured as a cell implantation aid for cartilage repair). Minimally invasive surgery (i.e., arthroscopic) surgery qualifies; however, injections of liquefied substances (even if they contain cells) through needles are not included in "surgery" as used herein.

Hyaline cartilage includes any type of cartilage that presses and slides against another segment of cartilage in an "articulating" manner (i.e., which normally is lubricated by synovial fluid) in an articulating joint. It does not include cartilage of the type that forms spinal discs.

As used herein, for brevity and convenience, the term "hyaline cartilage" is deemed to also include the meniscal cartilage segments that are found in knee joints, and the labral cartilage segments that are found in hip and shoulder joints. Meniscal and labral cartilage segments have three traits that distinguish them from the type of true hyaline cartilage that directly covers a bone surface. Those three traits are:

(1) meniscal and labral cartilage segments have substantially thicker cross-sections, compared to the relatively thin layers of hyaline cartilage which form a direct coating on a "condyle" surface of a bone. In general, a hyaline cartilage coating, which functions as a lubricated protective surface, is comparable to a coat of paint, on a piece of wood, and it needs to be thin, to reduce the chance that it will become damaged or torn. By contrast, the role and purpose of the much thicker meniscal and labral segments of cartilage is to keep the bones within a movable-but-constrained path of motion, within a complicated joint (i.e., the knees, the hips, and the shoulders).

(2) As a direct result of the point made above, the meniscal and labral cartilage are made from a different type of cartilage (called fibro-cartilage) which has much longer internal reinforcing protein strands than hyaline cartilage; and, (3) meniscal and labral cartilage have different supporting structures, to attach those longer, thicker, more complex segments to their supporting bones, compared to hyaline cartilage.

Nevertheless, meniscal and labral cartilage segments are crucial components of the knee, hip, and shoulder joints, and because of the frequency of injuries to meniscal or labral cartilage, any surgeon who repairs knee, hip, or shoulder joints must and will be able to work on meniscal or labral cartilage. Therefore, the same types of kits disclosed herein for repairing hyaline cartilage will be equally useful for repairing injured or damaged meniscal or labral cartilage, and any references herein to procedures or kits for repairing hyaline cartilage are merely shortened for convenience, and to avoid repetition, and are intended to also apply to repair of (and to kits for repairing) meniscal or labral cartilage segments, as well.

Accordingly, one object of this invention is to disclose improved types of surgical kits that can make it easier to surgeons to rapidly and reliably carry out hyaline, meniscal, or labral cartilage repairs involving transplanted cells and biological materials, rather than just mechanical parts.

Another object of this invention is to disclose improved surgical kits that are specifically optimized for handling hyaline or meniscal cartilage repairs that utilize placental membrane segments.

These and other objects of the invention will become more apparent through the following summary and description.

SUMMARY OF THE INVENTION

Surgical tools and kits are disclosed for repairing hyaline or meniscal cartilage, using membrane segments to protect and promote the growth and activity of cartilage-generating cells. These types of surgical kits include:

(i) a set of dilator tubes, adapted from similar types of dilator tubes that currently are used in some types of spinal surgery, that will allow a surgeon to progressively enlarge an insertion tunnel that will be used to insert a membrane segment into an articulating joint that is being surgically repaired; and, (ii) at least one (and preferably an assortment of) membrane "tamping" devices, each having a rounded and smooth "tamping head" (or actuator tip, or similar terms) mounted at the end of a handle, with a size and length that allow the working tip of the tamping tool to pass through the longest dilator tube in the kit while being firmly held by the surgeon.

Additional components (including disposable supplies) that can help facilitate the types of surgery described herein can also be included in any such surgical kit, or in "supplemental" kits that can be bundled and shipped together with a "primary" kit as described herein.

DETAILED DESCRIPTION

Surgical kits are disclosed which are optimized for use during surgical repair of hyaline or meniscal cartilage, using transplanted cells and biological materials, rather than just mechanical parts.

The essential (or "first tier") components in any such kit include a set of dilator tubes and a set of "membrane tamping devices", as described below. Additional and/or supplementary components also can be included in such a kit if desired, to increase the utility and helpfulness of such kits at only modest expense. However, such components are not essential, and the types of tools and supplies that can be included normally would be in the possession of most well-supplied hospitals and surgical clinics.

Figure 1:
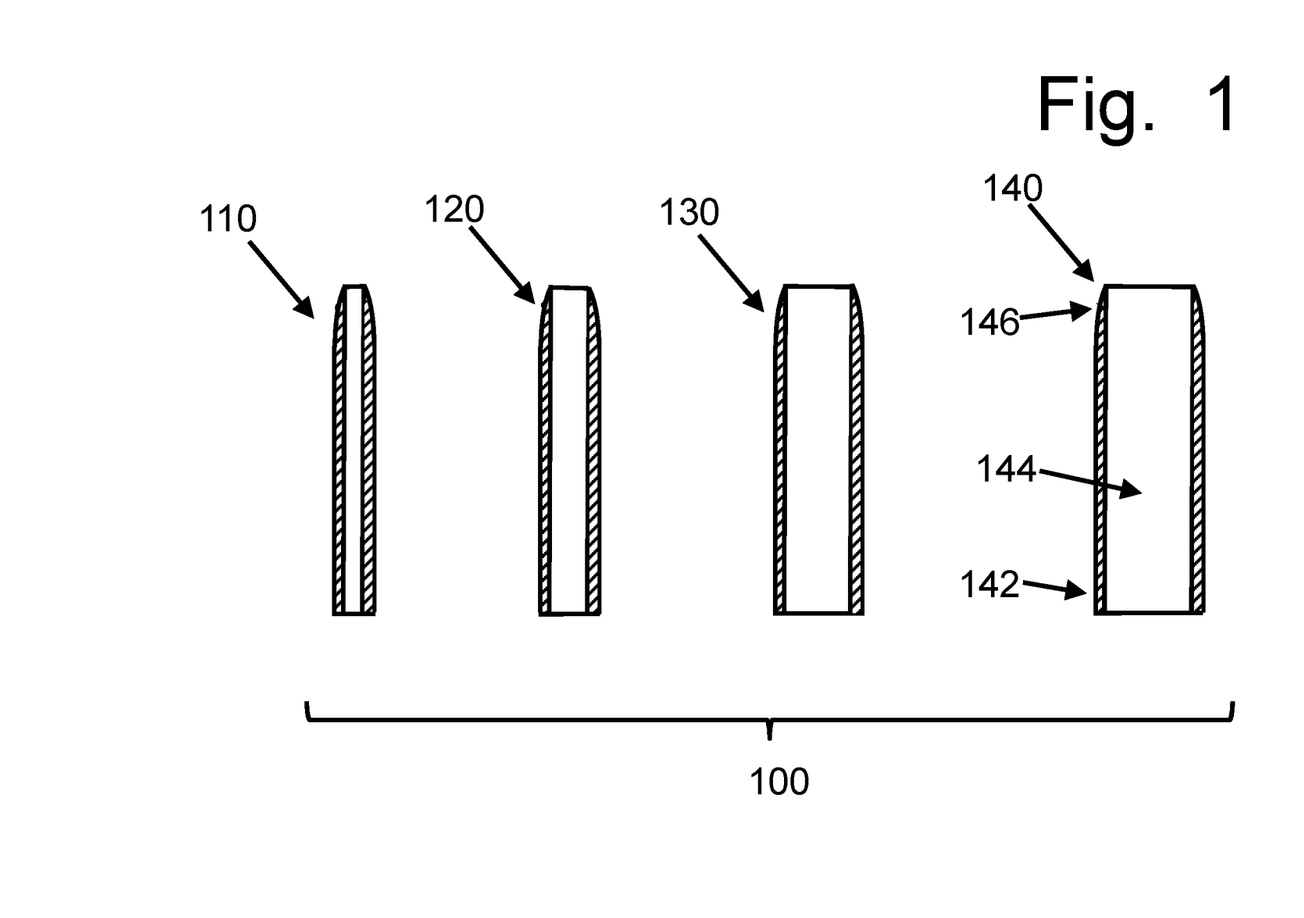
FIG. 1 contains cross-section views of a series of progressively larger dilator tubes, with each successive tube sized to slide over the next smaller tube while being pressed into an arthroscopic surgery incision, and with each tube having smooth rounded shoulders to minimize tissue damage as it is pushed into a joint that is being repaired.

Accordingly, the essential components in the new types of surgical kits described herein include a set of dilator tubes. Examples of such tubes are illustrated in FIG. 1, in which a complete set 100 is made up of four such tubes with increasingly larger diameters, identified as tubes 110 through 140 in FIG. 1. All four tubes are illustrated, in FIG. 1, as cutaway drawings, to indicate the cross-sectional shapes of their cylindrical walls. Each dilator tube, in a series of dilator tubes with increasing diameters, should be specifically designed to slide into a knee joint, smoothly and snugly over the outer surface of the previously-inserted, next-smaller dilator.

These dilator tubes are provided with a series of increasing diameters. As with hypodermic needles, electric wires, and various other elongated round objects, the "gauge" of a dilator tube refers to the outside diameter, measured as a fraction of an inch. A 20-gauge tube (or wire, or needle) will have an outside diameter of ½0th of an inch, while a 16-gauge tube will have an outside diameter of ⅟₁₆th of an inch. The smaller the gauge number, the larger the tube.

In tubes designed for use on adults, the smallest dilator tube can have a diameter of about 18 to 20 gauge, since that diameter is thin enough to allow its rounded and/or beveled tip to be pushed through a relatively small incision in the skin, until the tip of the dilator tube reaches the desired depth.

In most knee operations to repair damage to cartilage in the "femoral runners" (i.e., at the bottom end of the thighbone) and/or the "tibial plateau" (i.e., at the top of the shinbone), the patient will be lying on his or her back, and the knee will be flexed to a 90 degree angle, firmly strapped down to avoid any unwanted motion. The patient will receive spinal or a local or regional anesthesia during the operation, so that he or she will feel no pain or other sensations of any sort in the knee that is being operated upon, but will nevertheless remain conscious and awake (although usually sedated somewhat) throughout the operation.

The initial dilator insertion, involving the first and thinnest dilator tube, will be done by a surgeon with the aid of a "guidewire" having a tip made of an alloy or other material that will show up clearly on an imaging machine that can provide real-time video-type images, on a fluoroscope, ultrasound, or similar machine. It is presumed herein that the dilator tubes will be made of a polymer which creates a clear image on the monitor screen of a fluoroscope or ultrasound machine, so that the surgeon will know how deep a tube has reached, and how closely it is approaching the cartilage, at all times during insertion. If that is not the case, one or more bands, stripes, buttons, or other components made of imaging material can be embedded within the wall of the dilator, at or near the insertion tips of the dilator tubes.

Beyond those general comments, the level of skill pertaining to this invention is quite high, and relates to orthopedic surgeons who are fully experienced in arthroscopic surgery. Therefore, attention will focus solely on the kits herein, and it is not necessary to provide additional information on how arthroscopic surgery is performed.

The largest tube in a kit as described herein can have either: (i) a "default" diameter, such as 1, 1.2, or 1.5 cm; or, (ii) a diameter that will be specified by the surgeon, who will specify the largest tube that should be included in a specific kit intended for work on a specific patient, after the surgeon has used imaging technology to determine the size and shape of the cartilage defect(s) that need to be repaired in that patient's knee.

The cross-sectional structures of all four of the dilator tubes 110-140 are shown in FIG. 1. Because it is the easiest to illustrate, callout numbers showing the components are indicated on the largest dilator tube 140. The cylindrical outer wall 142 surrounds an open cylindrical channel 144 (which can also be called a tunnel, tube, port, access port, or any other suitable term).

The insertion tip 146 of the outer wall 142 should be tapered, beveled, or rounded, but without making the circular leading edge sharp enough to aggressively cut into tissue. This will help the circular leading edge push and stretch surrounding tissue out of the way with minimal damage, as the tube is being pushed and driven into a knee joint that is being repaired.

Unless test results prove that some other shape will cause less damage to soft tissue, a presumption arises that the interior surface of the cylindrical channel 144, at the insertion tip 146, should be completely cylindrical, and the beveled, tapered, or rounded surface which surrounds the insertion tip 146 should be provided by the outside surface of the dilator tube. This will allow the tapered edge, at the insertion end of each dilator tube in a series of progressively larger tubes, to "hug the wall" of the "next size smaller" dilator tube, during insertion, in a manner that will push soft tissue that is encountered, in a smooth and consistent outward direction, to the greatest extent possible, without any "catching", grabbing, or unwanted tearing of that soft tissue by the semi-sharp leading edge of each dilator tube.

If desired, the opposing end 148 (which can also be called the base, handle, or other suitable terms) of any dilator tube can be provided with one or more notches, grooves, or other coupling components, to allow a driving tool (which can have a shape comparable to a screwdriver handle, a wingnut, etc.) to be reversibly coupled to a dilator tube during the insertion process. This can provide the surgeon with a more secure and reliable way to rotate, rock back-and-forth, or otherwise move and manipulate any dilator tube in any way desired, to help push it through the membranes, tendons, ligaments, muscles, and other soft tissues around a knee joint, in ways that will minimize damage to those tissues.

Similar types of dilator tubes, but with lengths that are too long for optimal use in knee surgery, have been developed and sold by others, mainly for use in certain types of back surgery. Dilator tubes used in spinal work typically have lengths of at least 5 cm (about 2 inches), and lengths of 8 to 10 cm are common. By contrast, dilator tubes that are designed and intended for use in knee surgery should be substantially shorter, preferably in a range of about 3 to 4 cm.

That reduction in length has important effects and results, in the context of this particular invention, because of the need for ultra-precise surgical work on a cartilage surface, which will have its surface exposed at the far end of a dilator tube. If a surgeon can get his hands, fingers, and instrument grips closer to an actual cartilage surface which is being repaired, and does not have to do everything at the bottom end of a tube which is kept as narrow as possible in order to minimize tissue damage, then the surgeon will have a better "feel" for the actual work on the cartilage surface, and a better level of control.

Anyone can understand this point on a theoretical basis. Laymen can better understand and appreciate how important it actually becomes, on a practical level, if they will try to perform a simple task which requires precision, while using a set of tools that place their hands several inches away from the action zone. As one example, a layman can pick up a pen and use it to carefully sign his name, writing in as clear and legible a manner as possible; and then, he can use a pair of pliers to pick up that same pen and sign his name again, in the same careful way, via the pliers. When both are complete, the two signatures can be compared against each other, to see how the insertion of an additional tool into the process, and the extra distance between the hand and the paper, affected both the speed and performance of that task, and the quality of the work product.

Accordingly, it represents an important insight that dilator tubes should be developed for knee surgeries, which will resemble the types of dilator tubes developed for spinal surgery, but which must have a crucial difference in their lengths, compared to dilator tubes for spinal surgery.

Figure 2:
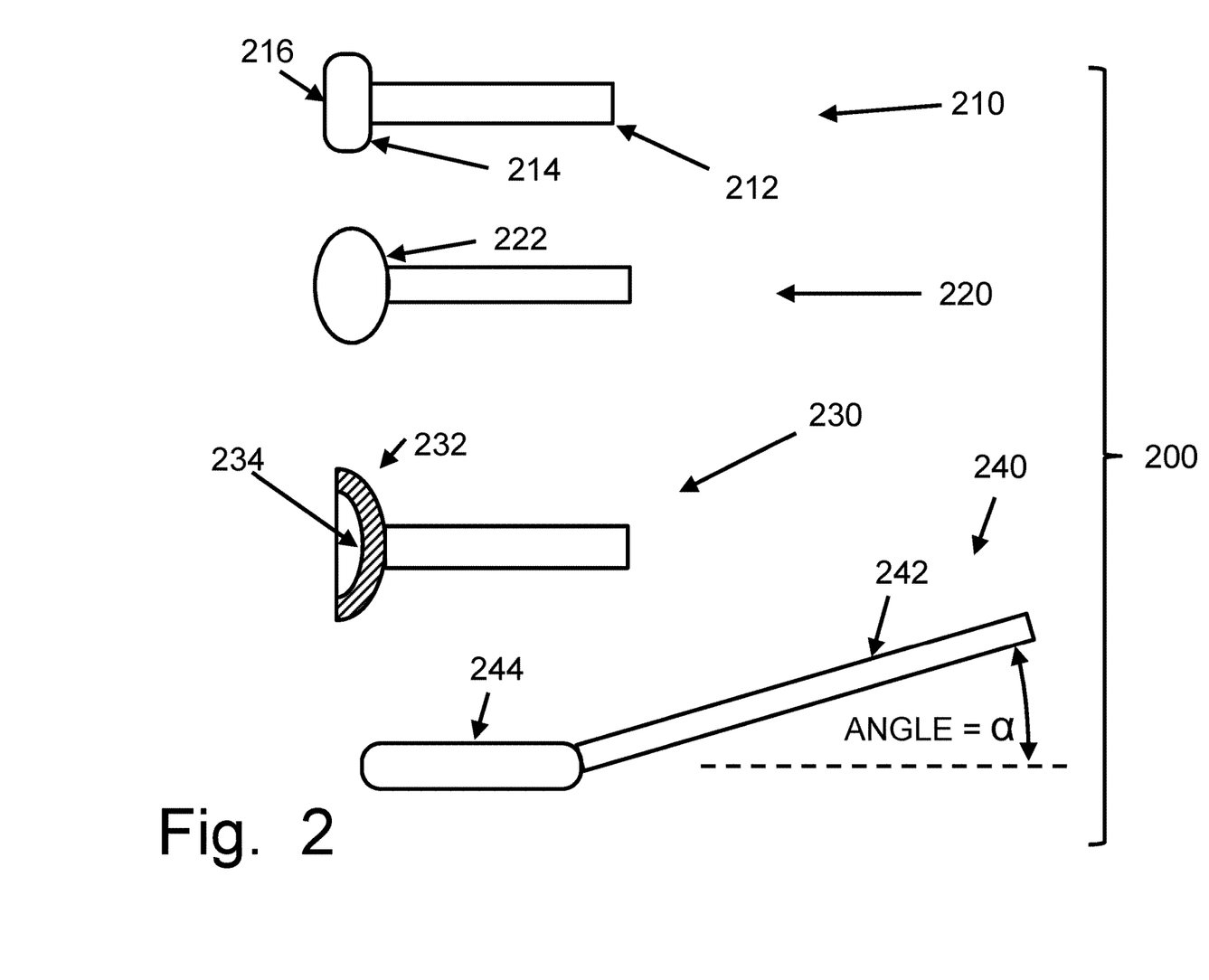
FIG. 2 depicts an assortment of tamping devices, with a variety of flat, convex, concave, and angled shapes that can be used to firmly press the entire surface of a placental, amniotic, or other repair membrane, onto as damaged cartilage surface that needs repair.

Moving on to the next set of items in a surgical kit as described herein, FIG. 2 depicts side views of four different "tamping tools" 210 through 240, all of which together comprise a "tamping tool set 200". All of these tamping tools are designed and intended to help a surgeon press a segment of a specialized cartilage repair membrane, in a gentle but firm and even manner, onto a damaged cartilage surface that is being repaired.

Tamping tools 210-230 are intended for use on a femoral runner which is being repaired. Each tool has a shaft 212, such as shaft 212 in tool 210, which also can be called a handle, grip, or similar terms. Any such shaft can have a round cross-section, if desired; alternately or additionally, they can have square, hexagon, triangular, or other geometric cross-sectional shapes, to provide surgeons with greater rotational control over a tool, especially for tools which have non-round heads.

Tamping tool 210 has a "head" 214 which provides a somewhat enlarged flat surface 216. That head component can also be called an actuator, tamper, or similar terms.

Tamping tool 220 has a more nearly spherical head 224, which will enable it to press membrane segments into valleys, troughs, depressions, and similar shapes. This tool can also be used in tamping a membrane onto a tibial plateau, as described below.

Tamping tool 230 has a head 232 with a concave tamping surface 234. Because of the shape of the highly convex surfaces of the "femoral runners" (which are shaped generally like two parallel rims on a pulley), most cartilage injuries on femoral runners occur on those highly exposed and vulnerable convex surfaces. Therefore, a tamping surface which has an accommodating concave shape, as indicated in tamping head 234 in FIG. 2, will be better suited for creating smoothly-distributed and even pressures, across convex cartilage surfaces, than a flat or spherical tamping surface as shown on tools 210 and 220.

Also shown in FIG. 2 is a tibial tamping tool 240, which is designed to help a surgeon press a cartilage repair membrane onto the surface of a cartilage segment known as the "tibial plateau". The tibial plateau covers the uppermost surface of the tibia (i.e., the shinbone). It has a relatively complicated shape, with two shallow concave surfaces (the one on the inner side of a knee joint is called the "medial" surface, or compartment, while the one on the outer side of the knee joint is called the "lateral" surface or compartment), separated from each other by a set of bony protrusions with a generally front-to-back (anterior-posterior) alignment. Those bony protrusions form the "tibial spine", which provides attachment points for a complex set of tendons and ligaments, and for the ends of the two segments of "meniscal" cartilage, which are thick arc-shaped segments that are generally wrapped around the two outer sides of the knee joint. Since any alterations to the bony protrusions in a tibial "spine" will lead to serious disruptions in those tendon, ligament, and meniscal attachments, surgeons always try, whenever possible, to leave a tibial spine alone (except in surgeries called "total knee replacements", or TKR's), even if they need to repair or replace both of the two shallow trays of a tibial plateau, located on the lateral and medial sides of a tibial spine.

Accordingly, tibial tamping tool 240 has a shaft/handle component 242 which is affixed to the head component 244 at a displacement angle, designated by the Greek letter alpha (α). A displacement angle of about 15 to about 20 degrees will be suitable for allowing a surgeon to insert the tamping head 244 through a dilator tube, without difficulty, and to then maneuver that tamping head down into the concave "tray"-like surfaces on a medial and/or lateral side of the tibial plateau, to allow the tamping head to press a cartilage repair membrane firmly into the concave shape of that tibial tray.

In addition, as mentioned above, the rounded-head tamping tool 220 can also be used for tamping a cartilage repair membrane onto a tibial plateau surface.

It is not yet clear, at the current stage of development and testing, which particular types and shapes of tamping tools will emerge as the most favored tools, among the surgeons who will use these kits; similarly, it is not yet known whether some surgeons might prefer one particular collection of tamping tools, while other surgeons might prefer a different collection. Accordingly, the claims herein refer to kits that contain "at least one femoral tamping tool", and "at least one tibial tamping tool". A presumption arises that, since these types of small and disposable tools are simple and inexpensive to manufacture, by simply molding a single small item from a suitable polymer, then any tamping tool should be included in a kit, if there is any significant likelihood that it might become useful and helpful, not all the time, but during special occasions, if and when a surgeon encounters an unanticipated problem, challenge, or difficulty during some particular operation on a knee.

Figure 3:
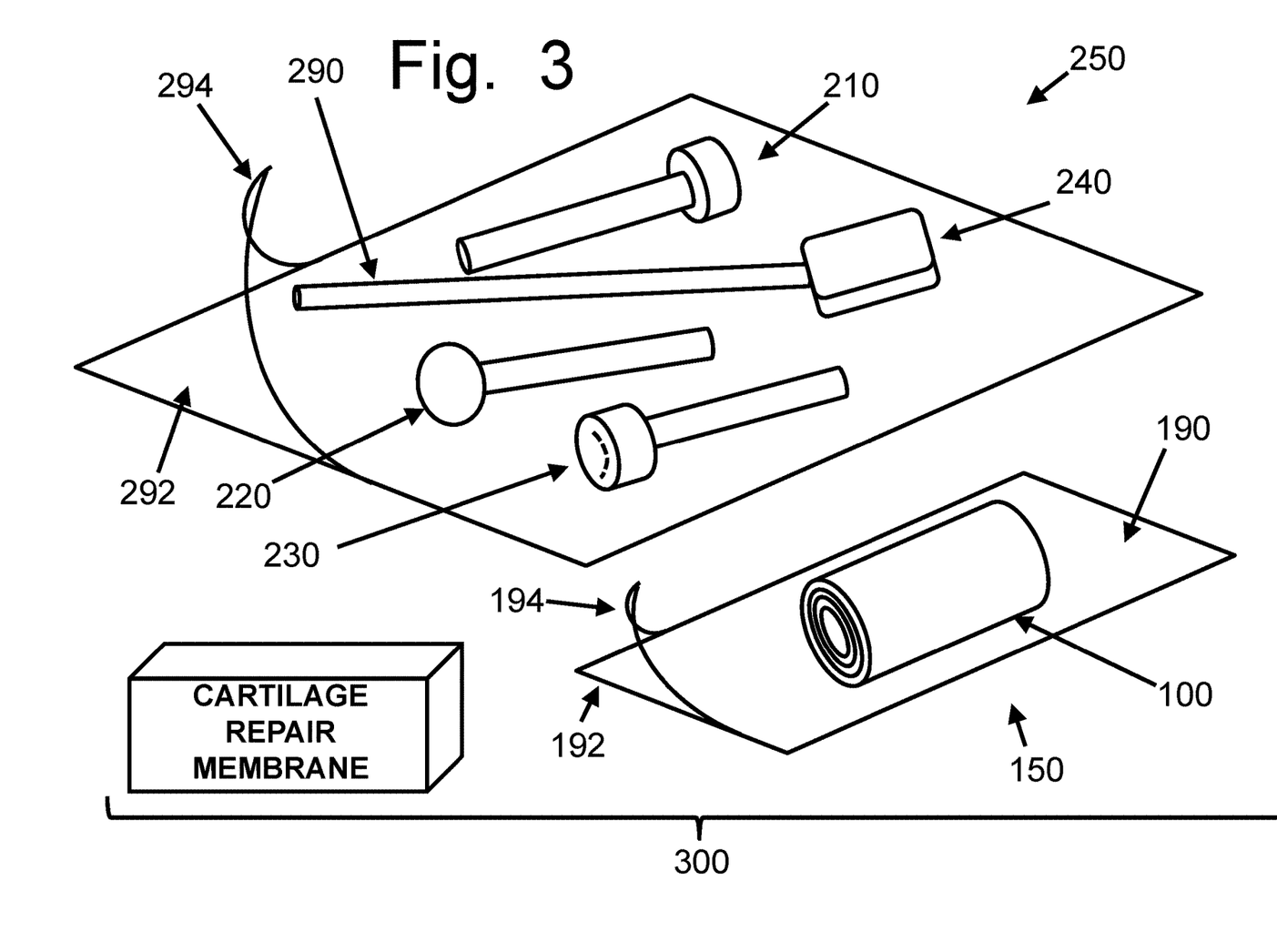
FIG. 3 depicts a surgical kit, containing a set of dilator tubes and tamping devices enclosed in sealed sterile envelopes, to provide surgeons with the tools, specialized reagents, and disposable supplies that they are likely to need during a cartilage repair operation involving placental, amniotic, umbilical, or other membranes.

Accordingly, FIG. 3 shows the components described above, assembled into a surgical kit 300. This kit comprises two different envelopes, designated as "dilator subassembly 150" (which contains the dilator tube set 100), and "tamping tool subassembly 250" (which contains a collection of tamping tools). The dilator envelope 190 is formed from a bottom (or backing) layer 192, and a top (or upper, or sealing) layer 194. Similarly, the tamping tool envelope comprises a bottom layer 292 and a top layer 294.

Both layers (in both envelopes) are made of watertight, gastight, microbe-proof plastic, and they are sealed together around their entire periphery, to create a complete and reliable sterile seal. The upturned envelope corners shown in FIG. 3 are solely for the purpose of illustrating both layers; if a sealed envelope of this type is ever opened inadvertently or at the wrong time, or if it becomes damaged, torn, or cut in a way that breaks the sterile seal, its value and contents will be effectively ruined, and its contents will need to be autoclaved, destroyed, or returned to the manufacturer.

Conventional practice is to make the upper layer out of clear plastic, so that anyone who looks at the envelope will be able to determine exactly what is inside it, without having to open it; conversely, it is conventional practice to make the bottom layer out of opaque plastic, so that there cannot be any visual confusion as to which or how many items are inside the top envelope only, if two or more envelopes happen to be stacked on top of each other or otherwise placed adjacent to each other.

Similarly, conventional practice is to manufacture such envelopes in a "vacuum packed" manner, so that if any air ever manages to enter the envelope (such as through a nick, cut, or defect which is too small to be seen), the "vacuum packed" appearance, feel, and texture will be lost, and will become a warning that the contents can no longer be guaranteed sterile.

In addition, kit 300 as illustrated in FIG. 3 also includes a separate sealed and sterile enclosure, in the form of a small box which is labeled as "Cartilage Repair Membrane". That outer enclosure (which can be a box, cylinder, or any other suitable shape, made of hard plastic, metal alloy, etc.) should have enough strength and stiffness to provide structural protection against unwanted forces (such as compression, shearing, etc.) or impacts that might damage the membrane. The outer protective enclosure normally will hold a sealed sterile envelope inside it, and the sealed inner envelope will hold a segment of placental or other membrane which will be used to help treat the cartilage defect in the knee joint which is being repaired.

Since that membrane segment is in its own separate sealed enclosure, it can be either: (i) included as a "direct" part of the kit described herein (i.e., within the same sealed envelope that holds the dilator tubes and/or tamping tools; or, alternately, (ii) treated as a distinct and optional component, which can be simply added (by a shipping clerk, an automated loading machine, etc.) to the same cardboard box or other shipping container that holds the kit(s) with the tubes and tools.

Figure 4:
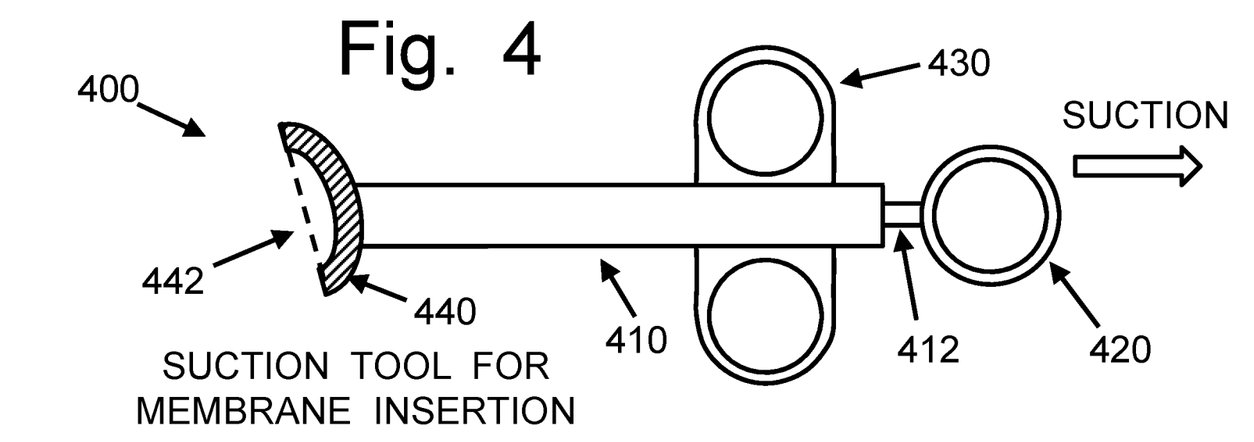
FIG. 4 depicts a type of insertion and placement tool with an actuator that can be withdrawn slightly, using a thumb ring, to create a mild vacuum across an actuator that is covered by a screen or perforated plate, to create a mild vacuum which will securely hold a membrane segment in place, on the actuator surface, while it is being inserted into a joint and then positioned on a cartilage surface.
Figure 5:
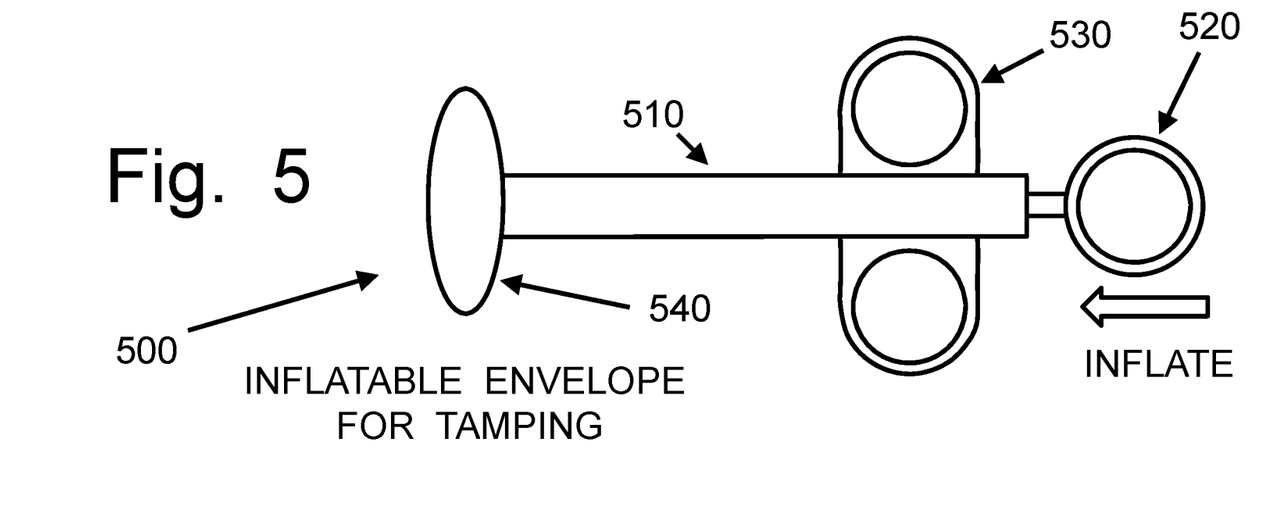
FIG. 5 depicts a tamping tool with an actuator balloon that can be inflated gently, by pushing in a thumb ruing, to create an evenly-distributed fluid pressure, which can be used to firmly but evenly press a membrane surface against a cartilage surface that is being repaired.

FIGS. 4 and 5 illustrate two more types of tools that are likely to become useful during the types of knee surgeries disclosed herein (and possibly for other types of surgeries, as well). Either or both of these can be included in a surgical kit that contains dilator tubes and/or tamping tools as described herein.

Suction Tool, for Membrane Insertion

FIG. 4 illustrates a suction tool 400, which can use gentle suction to firmly but temporarily mount (or secure, grip, couple, etc.) a small segment of membrane to the actuator end of the tool. The main components of this tool 400 include a hollow barrel 410, which encloses a movable plunger-type device 412 that can travel within the hollow barrel 410. The "working end" of that plunger is not shown in FIG. 4, since it is hidden inside barrel 410; generally, it should comprise a tip made of a flexible rubber or polymer material, preferably with one or more thin "fin" or ring components around its entire periphery, comparable to the rubber or soft polymer plunger tip in a standard hypodermic syringe, so that it can generate an effectively air-tight seal as it travels longitudinally through the length of the hollow barrel 410. The visible part of plunger 412, in FIG. 4, is a shaft component which is coupled at the visible end thumb ring 420. In addition, a pair of finger rings 430 is mounted on the outside of barrel 410, near its "back" end.

At the "actuator" end of suction tool 400, a slightly concave suction component 440 will have its opening (which presumably will be circular in most cases, but which can be elliptical or otherwise shaped for specific uses) covered by a flexible screen (woven from strands of polymer), perforated membrane, or any other permeable but preferably non-rigid surface material 442 which can readily allow passage of water or saline solution through that permeable surface 442. If desired, the actuator tip can be provided with a sliding-type or swiveling-type mechanism, which will allow the permeable surface 442 to be angled in one or more directions, relative to the barrel 410; alternately or additionally, two or more suction tools 400 with their permeable surfaces angled differently with respect to the barrel 410 (such as one tool with a 10 degree offset angle, and a second tool with a 20 degree offset angle, compared to an imaginary plane which is perpendicular to the tool barrel 410), can be provided in a surgical kit. This would allow a surgeon to choose whichever suction tool would be best suited for inserting a segment of membrane into a specific knee joint to repair a specific defect.

This arrangement will allow a surgeon to place two fingers through the two finger rings 430, in a manner which will provide the surgeon with full control over the placement, positioning, and travel of the suction tool, while at the same time using his thumb to pull outwardly against the thumb ring 420, in a manner which will cause the plunger, inside the barrel 410, to create and sustain gentle suction pressure (via a liquid held inside the barrel 410) on a membrane segment that is mounted on the actuator tip of the suction tool. Accordingly, this tool can be used to:

(1) submerge the actuator tip of the tool into a sterile liquid, and fill the barrel with that liquid;

(2) gently place the permeable surface 442 against a membrane segment that is floating in a liquid;

(3) use a slight pulling (or retracting, withdrawing, or similar terms) motion on the thumb ring 420, to create a gentle suction that will securely affix the membrane segment to the permeable surface 442;

(4) use the suction tool to insert the membrane segment through a dilator tube, and into a knee joint, and then position the membrane in an exact desired location where it will press against a cartilage defect; and, (5) exert a gentle inward-pushing pressure on the thumb ring 420, to release the membrane from the permeable surface 442, and to press that membrane segment directly against (and into) the cartilage defect that needs to be repaired.

Fluid-Filled Inflatable Tamping Tool

FIG. 5 illustrates another type of tool that is likely to become useful various types of knee surgery, and possibly in other types of surgeries as well.

This tamping tool 500 works in essentially the same way as the suction tool 400, described above, in terms of fluid handling, and the barrel and handle components for tool 400 and tool 500 can be the same components, if desired, with different actuator tips that can be quickly affixed to or removed from those barrel and handle components.

As suggested by the illustration in FIG. 5, imposing a pushing motion, on thumb ring 520, while the tool 500 is being held stationary by means of the paired finger rings 530, will drive a plunger deeper into barrel 510. This action will forcibly drive an additional quantity of liquid, held inside the barrel 510, into a flexible inflatable envelope 540 which is mounted at the actuator end of tool 500. Accordingly, this will allow a small inflatable sac to exert what will become, in essence, gently- and evenly-distributed pressure, against a membrane which is being pressed against and into a cartilage defect. That type of distributed fluid pressure is likely to be optimal and ideal, for allowing a surgeon to do everything possible to firmly press and secure a cartilage repair membrane against an area of damaged cartilage, in a manner which will give the patient the best possible chance of a full and complete cellular repair of his or her damaged cartilage, in a knee joint.

Guide Tools for Positioning Pins or Staples

Figure 6:
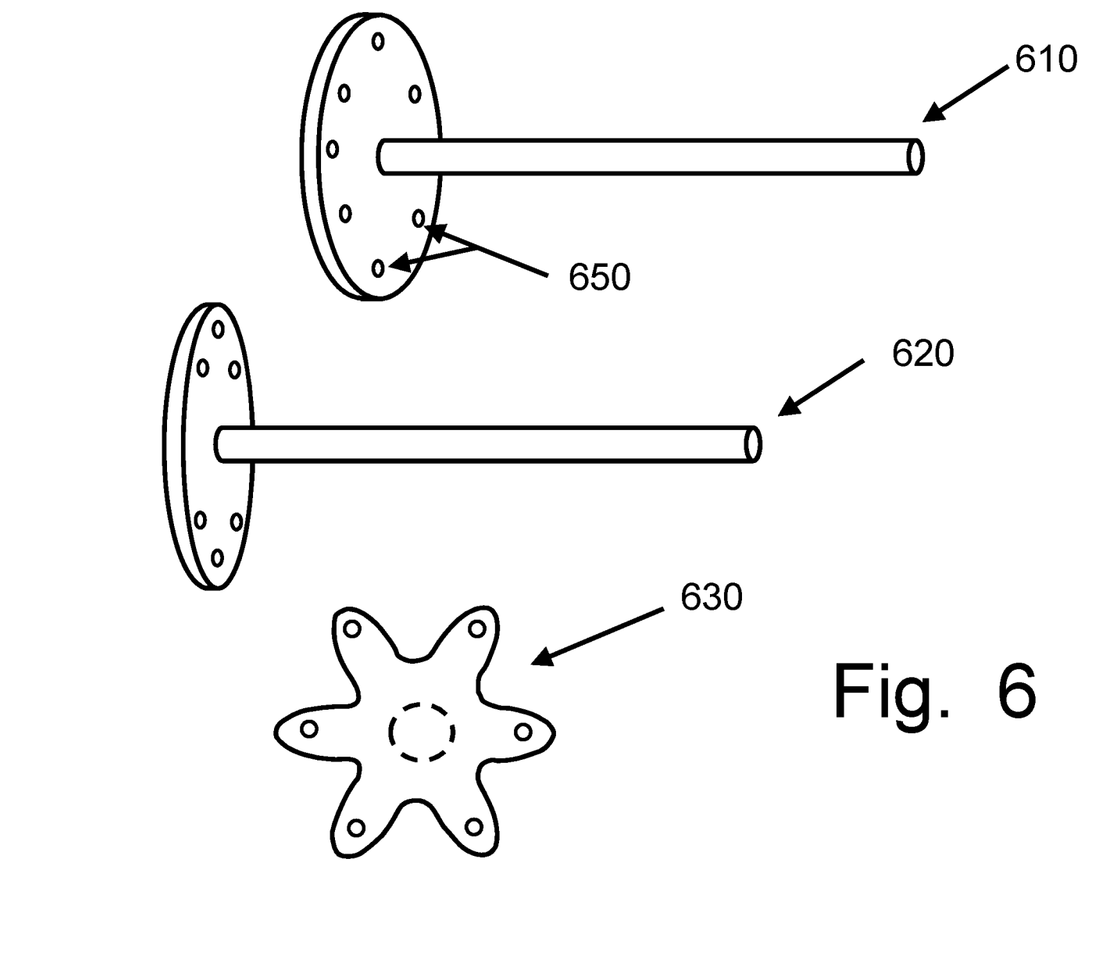
FIG. 6 depicts a set of three different guide tools, which can be used to help establish the placement of pins, staples, or other devices that are used to secure a membrane to a cartilage or bone surface that is being repaired.

FIG. 6 depicts three additional types of guide tools 610, 620, and 630, any or all of which may be useful in some types of cartilage repair procedures as described herein. Guide tool 610 contains a relatively wide working surface which has a generally round outer peripheral shape, while guide tool 620 has a generally oval (or elliptical) peripheral shape, and guide tool 630 has a classic "daisy" shape with a plurality of elongated "petal" components that can be pushed easily through an insertion tube while clustered together, and which then can spread out into a larger array when the tips of the "petals" emerge from the insertion tube.

Regardless of which particular shape is used in any specific surgical procedure, any of these guide tools will provide a plurality of guide holes 650, distributed around the outer peripheral edge of the guide tool. These holes can be used to help establish the desired placement, spacing, and position of any tacks, pins, or staples that are used to help secure a repair membrane to a damaged cartilage surface.

Optional and/or Supplemental Components

If desired, various additional types of surgical tools and/or disposable supplies can be either: (i) included within a surgical kit as described herein; or, (ii) packaged separately (but in comparable sterile packaging) in optional and/or supplemental kits that can be shipped routinely, whenever appropriate or desired, along with the types of specialized surgical kits described herein. The choice of whether to also send either: (i) an expanded surgical kit containing additional "optional" tools or supplies, and/or (ii) one or more supplementary kits, to accompany and support a limited set of specialized tools as described herein, will depend on the locale, context, and "level of support" where the anticipated surgery is to be performed. For example, additional conventional surgical tools are not likely to be needed, in an orthopedic surgery suite in a hospital or specialty clinic where orthopedic surgeries are performed each day; by contrast, if a doctor in a remote rural setting or less-developed country intends to perform this type of surgery, he or she is much more likely to need various additional tools and disposable supplies, to help ensure that every step of an intended procedure can be completed in the manner desired, without having to "scramble" and improvise various half-measures to make up for less-than-ideal tools and supplies.

Accordingly, companies that manufacture and sell these types of surgical kits to doctors in various different regions and localities around the US, and around the world, can incorporate any additional tools and/or supplies into either the sealed-and-sterile types of surgical kits described herein, or into supplement-type kits that can be bundled and shipped along with the surgical kits described herein.

The comments above apply in particular to various types of devices that can be used by surgeons to secure a membrane in place, in a manner which will "anchor" the membrane to a cartilage and/or bone surface, for a sufficient period of time to allow a surgically repaired segment of hyaline, meniscal, or labral cartilage to heal and/or regenerate properly (or to at least advance a sufficient distance along a pathway toward healing and/or regeneration), while the membrane remains in place in intact form.

Accordingly, such kits or supplementary kits can include any combination and number of pins, tacks, staples, suture strands, or other "securing devices", which can be made of either "resorbable" materials (i.e., materials that will gradually be degraded by bodily fluids, releasing biocompatible small molecules, over a span of time usually measured in days or weeks) or non-resorbable materials.

While most such devices are well-known and have been in use for decades, it also should be mentioned that another relatively new class of small surgical devices that are likely to be useful in the types of surgeries described herein have been disclosed recently. These devices are described in more detail in published US patent applications 2013/0190815 and 2014/0135834, both invented by Mansmann. Since they are not yet commercially available or well-known, they merit a brief mention and description herein.

These small devices can be called "knotless racheting suture anchors." As implied by the term "rachet", which is well-known in mechanical engineering and tool design, a racheting suture anchor will allow a suture strand to be pulled through the anchoring device in one direction, but it will grip the suture strand in a manner which will not allow the strand to be pulled back through the device in the opposite direction.

Accordingly, several such devices, each one gripping a single suture strand, at various locations around a membrane segment that is being inserted into a joint, can allow a surgeon to take each of several suture strands through a stepwise procedure that can be referred to as "start, then snug, then tighten". This phrase indicates that each suture strand can be initially started (i.e., coupled to a racheting device that has been anchored to bone or tissue at a desired location), without any tension being imposed on it, as part of the initial insertion of a membrane segment into an articulating joint. The membrane segment in most cases will be in rolled-up cylindrical form, to allow it to pass through an insertion tube. After it enters the joint, the membrane segment is unrolling (or "unfurled", or similar terms), in a manner which roughly approximates the final placement of the membrane. At that point, several suture strands can be attached to the membrane, at suitable locations around its periphery, and each strand can then be "threaded" through a racheting anchor, in a manner comparable to threading a needle; alternately, the suture strands can already be coupled to the rachet anchoring devices, and their "free ends" can be attached to the membrane segment.

After all of the suture strands have been "started", the surgeon will then "snug" each one, usually by selecting two strands on opposite sides of the membrane segment for the first two "snugging" steps. During this stage, each suture strand will be tightened, by use of its racheting anchor device, to a reduced and non-final level of tension, to make sure that everything is properly positioned, before a final series of tightening and tensioning steps is commenced.

After all of the suture strands have been "snugged" to a desired level of modest tension, the surgeon can then begin tightening all of them, in any desired sequence (again, usually by selecting two strands on opposite sides of the membrane segment, for the first two tightening steps. A typical tightening operation is likely to go through at least two or three cycles, such as by taking each and all of the strands to a "50% of final" level of tension, then taking all of them to an "80% of final" level of tension, and then taking all of them to the desired final level of tension, with a brief checking and confirmation step between each cycle of increasing tension levels.

Accordingly, a set of small racheting suture anchors, properly secured to nearby bone surfaces (for repair of hyaline cartilage segments, such as femoral runner or tibial plateau surfaces) and/or encapsulating tissue (for repair of meniscal or labral cartilage segments), and located away from the surfaces where cartilage surfaces actually rub and slide against each other, can be very useful for helping surgeons position and then anchor membrane segments in the exact desired locations, in articulating joints that need to be repaired.

Visualization of Arthroscopic Tools and Devices

The types of surgical tools described herein are used with the help of imaging devices that display "live-action" images (i.e., images which show current conditions at any given moment, as opposed to pre-recorded images which involve delays between creating and displaying an image). The two main types of "live-action" imaging machines that are used during most types of arthroscopic or other minimally-invasive surgery involve either of two different mechanisms or systems. Those are:

(i) ultrasound devices, which are most familiar to most readers in the context of creating images of a fetus inside a pregnant woman, and which also can be used with arthroscopic or laparoscopic tools, if the tips of the tools are provided with "bands" of specialized material insets that will generate clear images during an ultrasound-guided procedure; and, (ii) fluoroscopes, which create images that are similar to X-rays pictures, except in live-action video-type form. In X-ray or fluoroscopic images, any device made of metal will appear generally opaque; that makes it easily visible, when surrounded by semi-transparent X-ray-type images of soft tissues and bones.

Accordingly, any tool or device described herein can be made of (or "labeled with", such as by placement of specialized "bands" or insets, at or near an actuator tip) materials that are specifically selected to enable clear visualization, while in use and while inside a limb, extremity, or body of a patient, by ultrasound and/or fluoroscopic machines.

It also should be noted that most arthroscopic operations are performed with a live video feed which the surgeon can see at any time. The video images are created by a miniaturized video camera lens, affixed to the end of handle-type device, which uses a fiber-optic cable to transfer the images from inside the joint, to a computer or TV monitor. When arthroscopic work is being done on any of the larger articulating joints (which includes knees, hips, and shoulders), the joint usually is expanded and "opened up", to give the surgeon more room to work, by injecting clear saline solution into it under a mild pressure, and by keeping clear transparent liquid flowing slowly through the joint during the course of the surgery, to carry out blood, debris, etc. Accordingly, if the tips of surgical tools and devices are painted with in non-red colors (such as yellow) which will remain visible even in the presence of some quantity of diluted blood, the surgeon can more easily see those tool tips, on a TV or computer monitor.

Thus, there has been shown and described a new and useful set of tools, devices, and articles of manufacture, for enabling improved repairs of damaged or diseased cartilage segments, in knee joints. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

EXAMPLES

Example 1: A surgical kit for use in cartilage repair surgery on mammalian knee joints, comprising:
  a. a plurality of dilator tubes which are designed and sized to enable successively larger dilator tubes to be inserted into a knee joint through a skin incision until a working dilator tube having an internal opening at least I centimeter wide provides access to at least one damaged cartilage surface, wherein said working dilator tube has a length of less than 4 centimeters; and,
  b. at least one tamping tool having an elongated handle and at least one tamping component coupled to said handle, wherein said tool is designed, sized, and shaped to enable a surgeon to insert said tamping component through said working dilator tube, and to use said tamping component to press a repair membrane firmly against a damaged surface of a cartilage segment in an articulating joint, wherein each of said dilator tubes and tamping tool is contained within at least one sealed enclosure which will maintain sterility of said tubes and tool.

Example 2: The surgical kit of example 1, wherein a plurality of tamping tools is contained within at least one sealed enclosure, including at least one tamping tool having a concave tamping surface, at least one tamping tool having a convex tamping surface, and at least one tamping tool having a tamping surface that is affixed at an oblique angle relative to said elongated handle.

Example 3. The surgical kit of example 2 wherein said plurality of tamping tools includes at least one tool which enables a surgeon to create gentle suction at an actuator end of said tool, sufficient to firmly hold a membrane segment in place on said actuator end of said tool while said membrane segment is being emplaced on a damaged cartilage surface in an articulating joint that is being repaired.

Example 4. The surgical kit of example 2 wherein said plurality of tamping tools includes at least one tool which enables a surgeon to expand and enlarge an inflatable component at an actuator end of said tool.

Example 5. The surgical kit of example 2 wherein said plurality of tamping tools includes at least one tool which comprises an actuator component which contains a plurality of orifices located near a peripheral edge of said actuator component.

Example 6. The surgical kit of example 2 wherein all tamping surfaces on all tools are made of yielding non-rigid materials.

Example 7. The surgical kit of example 1, wherein said dilator tubes having incremental diameters comprise:
  a. a first insertion tube having an external diameter no greater than 16 gauge; and,
  b. a plurality of expansion tubes, wherein each expansion tube has a beveled or tapered insertion end and is designed and sized to slide smoothly, lengthwise, along an outer surface of a smaller expansion tube, in a manner which allows each expansion tube to be pushed into a tissue opening which is being enlarged, in a manner which pushes soft tissues out of its pathway without cutting into said soft tissues.

Example 8. The surgical kit of example 7, wherein said working dilator tube has a length of less than 3 centimeters.

The invention claimed is:

1. A surgical kit for use in cartilage repair surgery, the surgical kit comprising:
  a. a plurality of dilator tubes comprising incremental diameters designed and sized to enable successive dilator tubes of the plurality of dilator tubes to be inserted into an articulating knee joint through a tissue opening until a working dilator tube of the plurality of dilator tubes is inserted through the tissue opening to provide access to at least one damaged cartilage surface of the articulating knee joint, wherein said working dilator tube has a length of less than 4 centimeters and an internal opening of at least 1 centimeter; and,
  b. a plurality of tamping tools having an elongated handle and at least one tamping component coupled to said elongated handle, wherein said at least one tamping component is designed, sized, and shaped to be inserted through the internal opening of said working dilator tube and to press a repair membrane against the at least one damaged cartilage surface, the plurality of tamping tools comprising:
    at least one first tamping tool having a concave tamping surface on a tamping component of the first tamping tool, the concave tamping surface designed, sized, and shaped to press the repair membrane against a femoral runner; and
    at least one second tamping tool having a convex tamping surface on a tamping component of the second tamping tool, the convex tamping surface designed, sized, and shaped to press the repair membrane against the tibial plateau; and
    at least one third tamping tool having an oblique tamping surface on a tamping component of the third tamping tool, the oblique tamping surface is affixed at an oblique angle relative to an elongated handle of the third tamping tool,
    wherein the concave tamping surface, the convex tamping surface, and the oblique tamping surface are made of yielding non-rigid materials.

2. The surgical kit of claim 1 wherein the elongated handle of a fourth tamping tool comprises a hollow barrel and the fourth tamping tool further comprises:
  an actuator end operatively coupled to the hollow barrel, the actuator end comprising an opening in fluid communication with the hollow barrel; and
  a plunger positioned within the hollow barrel, the plunger configured to create suction at the actuator end, the suction sufficient to hold the repair membrane on said actuator end of said fourth tamping tool while said repair membrane is being emplaced on the at least one damaged cartilage surface.

3. The surgical kit of claim 2, wherein the actuator end is concave.

4. The surgical kit of claim 2, wherein the fourth tamping tool further comprises a permeable surface covering the opening of the actuator end.

5. The surgical kit of claim 1 wherein the elongated handle of a fourth tamping tool of the plurality of tamping tools comprises a hollow barrel and the fourth tamping tool further comprises:

an actuator end operatively coupled to the hollow barrel, the actuator end comprising an inflatable component; and a plunger positioned within the hollow barrel, the plunger configured to enlarge the inflatable component.

6. The surgical kit of claim 5, further comprising a liquid positioned within the hollow barrel.

7. The surgical kit of claim 1 further comprising a guide tool comprising a plurality of guide holes located near a peripheral edge of the guide tool.

8. The surgical kit of claim 7, wherein each of the plurality of guide holes is configured to guide a fastener to secure the repair membrane to the at least one damaged cartilage surface.

9. The guide tool of claim 7, wherein the guide tool comprises a shape selected from the group consisting of a generally round shape, a generally oval shape, and a daisy shape.

10. The surgical kit of claim 1, wherein said plurality of dilator tubes further comprises:
    a. a first insertion tube having an external diameter no greater than 16 gauge; and,
    b. a plurality of expansion tubes, wherein each expansion tube has a beveled or tapered insertion end and is designed and sized to slide lengthwise along an outer surface of a smaller one of the plurality of expansion tubes or the first insertion tube, in a manner which allows each expansion tube to be pushed into soft tissues of the tissue opening in order to enlarge the tissue opening without cutting into said soft tissues.

11. The surgical kit of claim 1, wherein said working dilator tube has a length of less than 3 centimeters.

12. The surgical kit of claim 1, wherein each of the plurality of dilator tubes and the plurality of tamping tools is contained within at least one sealed enclosure to maintain sterility of the plurality of dilator tubes and the plurality of tamping tools.

13. The surgical kit of claim 1, further comprising the repair membrane and the repair membrane is selected from the group consisting of placental membranes and collagen-derived membranes.

14. A surgical kit comprising:
    a plurality of dilator tubes comprising incremental diameters, the plurality of dilator tubes comprising a working dilator tube comprising a length of less than 4 centimeters and an internal opening of at least 1 centimeter; and
    a plurality of tamping tools, each tamping tool having an elongated handle and at least one tamping component coupled to said handle, wherein each tamping component is designed, sized, and shaped to be inserted through the internal opening of the working dilator tube, the plurality of tamping tools comprising:
        at least one first tamping tool having a concave tamping surface on a tamping component of the first tamping tool, the concave tamping surface designed, sized, and shaped to press a repair membrane against a femoral runner; and
        at least one second tamping tool having a convex tamping surface on a tamping component of the second tamping tool, the convex tamping surface designed, sized, and shaped to press the repair membrane against the tibial plateau;
        at least one third tamping tool having an oblique tamping surface on a tamping component of the third tamping tool, the oblique tamping surface is affixed at an oblique angle relative to an elongated handle of the third tamping tool,
        wherein the concave tamping surface, the convex tamping surface, and the oblique tamping surface are made of yielding non-rigid materials.

15. The surgical kit of claim 14, wherein the plurality of dilator tubes further comprise:
    a first insertion tube having an external diameter no greater than 16 gauge; and
    a plurality of expansion tubes, wherein each expansion tube has a beveled or tapered insertion end and is designed and sized to slide along an outer surface of a smaller one of the plurality of expansion tubes or the first insertion tube.

16. The surgical kit of claim 14 further comprising a guide tool comprising a plurality of guide holes distributed along the periphery of the guide tool configured to guide a fastener.

* * * * *